US007109241B1

(12) United States Patent
Richter et al.

(10) Patent No.: US 7,109,241 B1
(45) Date of Patent: Sep. 19, 2006

(54) ANTIMICROBIAL COMPOSITIONS FORMULATED FOR USE IN COLD TEMPERATURE CONDITIONS AND METHODS OF USE THEREOF

(75) Inventors: Francis Lawrence Richter, Lino Lakes, MN (US); Duane Joseph Reinhardt, Maplewood, MN (US)

(73) Assignee: Ecolab, Inc., St. Paul, MN (US)

( * ) Notice: Subject to any disclaimer, the term of this patent is extended or adjusted under 35 U.S.C. 154(b) by 229 days.

(21) Appl. No.: 09/676,620

(22) Filed: Oct. 2, 2000

(51) Int. Cl.
*A61K 31/23* (2006.01)

(52) U.S. Cl. .................................... 514/552; 514/558
(58) Field of Classification Search ................ 514/552, 514/558
See application file for complete search history.

(56) References Cited

U.S. PATENT DOCUMENTS

| | | | |
|---|---|---|---|
| 3,066,071 A | 11/1962 | Akers et al. | |
| 3,222,252 A | 12/1965 | Kraus | |
| 3,728,449 A | 4/1973 | Cantor et al. | |
| 3,993,777 A | 11/1976 | Caughman et al. | |
| 4,049,830 A | 9/1977 | Pugliese | |
| 4,113,854 A | 9/1978 | Andrews et al. | |
| 4,271,149 A | 6/1981 | Winicov et al. | |
| 4,404,040 A | 9/1983 | Wang | |
| 4,410,442 A * | 10/1983 | Lucas et al. ............... 252/107 | |
| 5,208,257 A * | 5/1993 | Kabara ...................... 514/552 | |
| 5,234,719 A | 8/1993 | Richter et al. | |
| 5,308,868 A | 5/1994 | Kefford | |
| 5,310,549 A | 5/1994 | Bull | |
| 5,368,868 A | 11/1994 | Winicov | |
| 5,462,714 A | 10/1995 | Talwalker et al. | |
| 5,503,838 A | 4/1996 | Schmidt et al. | |
| 5,529,770 A | 6/1996 | McKinzie et al. | |
| 5,534,266 A | 7/1996 | Ricketts | |
| 5,569,461 A * | 10/1996 | Andrews .................... 424/405 | |
| 5,618,841 A | 4/1997 | Kross | |
| 5,720,984 A | 2/1998 | Ricketts | |
| 5,885,620 A | 3/1999 | Foret | |

FOREIGN PATENT DOCUMENTS

| | | |
|---|---|---|
| DE | 231 065 A1 | 12/1985 |
| EP | 0 864 672 A1 | 9/1998 |
| EP | 0 906 724 A1 | 4/1999 |
| GB | 1144637 | 3/1969 |
| GB | 1561423 | 2/1980 |
| WO | WO 96/39839 | 12/1996 |
| WO | WO 99/18978 | 4/1999 |
| WO | WO 99/56757 | 11/1999 |
| WO | WO 00/13506 | 3/2000 |
| WO | WO 00/13507 | 3/2000 |

OTHER PUBLICATIONS

A. John Bramley et al, "Current Concepts of Bovine Mastitis," The National Mastitis Council, Fourth Edition, pp. 1-64 (1996).
F. H. Dodd et al., "Mastitis—The Strategy of Control," J. Dairy Science, 52(5):689-695 (1969).
F. H. Dodd et al., "Masitits Control," The Veterinary Annual pp. 21-62 (1970).
R. J. Eberhart et al., "Evaluation of a Hygiene and Dry Period Therapy Program for Mastituts Control," J. Dairy Sci., 55(12): 1683-1691 (1972).
R. J. Farnsworth, "Role of Teat Dips in Mastitis Control," J. Am. Vet. Med. Assoc., 176(10):1116-1118 (1980).
F. A. Murdough, et al., "Evaluation of 57 Teat Sanitizers Using Excised Cow Teats," J. Dairy Sci., 76(7):2033-2038(1993).
Roger P. Natzke, "Role of Teat Dips and Hygiene in Mastitis Control," J. Am. Vet. Med. Assoc. 170(10):1196-1198(1977).
F. K. Neave et al., "A Method of Controlling Udder Disease," Vet. Rec., 78(15):521-523 (Apr. 1966).
F. K. Neave et al., "Control Of Mastitis in the Dairy Herd by Hygiene and Management," J.Dairy Sci., 52(5):696-707(1969).
J. W. Pankey et al., "Uptake on Postmilking Teat Antisepsis," J. Dairy Sci. 67(6) 1336-1353(1984).
W. N. Philpot et al., "Hygiene in the Prevention of Udder Infections V. Efficacy of Teat Dips Under Experimental exposure to Mastitis Pathogens," J. Dairy Sci., 61(7):956-963(1978).
W. N. Philpot, "Control of Mastitis by Hygiene and Therapy," J. Dairy Sci., 62(1):168-176(1979).
W. N. Philpot et al., "Hygiene in the Prevention of Udder Infections III. effectiveness of 59 Teat Dips for Reducing Bacterial Populations on Teat Skin," J. Dairy Sci., 58(2):209-216(1975).
W. D. Schultz et al., "Effectiveness of Postmilking Teat Dips," J. Dairy Sci., 55(4): 426-3431.
D.P. Wesen et al., " Effectiveness of a Post-Milking Teat Dip n Preventing New Udder Infections," J. Dairy Sci., 58(10): 1391-1403.
L.K. Fox, "Colonization of *Stephylococus aureus* on Chapped Skin: Effect of Iodine and Chlorhexidine Postmilking Teat Disinfectants," J. Dairy Sci 75:66.
J.J. Goldbert et al., "Evaluation of Teat Conditioning Qualities of Postmilking Teat Dips," National Mastitis Council Technology Transfer Session, Orlando Florida, 1994.
M.D. McKinzie et al., "The Effect of Teat Skin Condition on Milk Yield and Milkout Time," National Mastitis Council Annual Meeting Proceedings (1995) p. 160-162.
M.A. Stillman et al., "Relative Irritancy of Free Fatty Acids of Different Chain Length," Contact Dermatitis 1975:1: 65-69.

* cited by examiner

*Primary Examiner*—Christopher S. F. Low
*Assistant Examiner*—C. Delacroix-Muirheid
(74) *Attorney, Agent, or Firm*—Merchant & Gould P.C.

(57) ABSTRACT

Antimicrobial compositions containing a carboxylic acid, for example, a fatty acid, and a carrier medium including a freezing point depressant are disclosed. The compositions can be formulated for use as a teat dip, for use on milk producing animals. In one particularly advantageous embodiment, a composition is formulated as a teat dip and includes suitable emollients, skin conditioners and lubricants.

30 Claims, No Drawings

ANTIMICROBIAL COMPOSITIONS FORMULATED FOR USE IN COLD TEMPERATURE CONDITIONS AND METHODS OF USE THEREOF

FIELD OF THE INVENTION

The present invention is directed to antimicrobial compositions having specialized benefit of skin protection and conditioning for the control of mastitis in milk producing animals that is especially useful in cold temperature environments and a method of treating for mastitis in cold temperature conditions. Furthermore, in some embodiments, the invention provides mastitis treatment compositions and formulations having specialized benefit of skin protection and conditioning on the teats of an animal that are already in poor health. In one preferred embodiment, the invention provides teat dip formulations comprising a carboxylic acid, typically a fatty acid, and a carrier medium including a freezing point depressing component.

BACKGROUND OF THE INVENTION

Mastitis is an inflammation of the mammary gland. Bovine mastitis is the most common and most costly disease affecting dairy herds. Some estimates suggest at least half of the dairy animal population having some degree or form of mastitis. This condition results in lowered milk yield and reduced milk quality. Economic loss to mastitis in the U.S. is estimated at about $1.8 billion or approximately 10% of total milk sales with about two-thirds of this loss due to reduced milk production from infected cows. In dairy cattle, mastitis typically results from microorganisms; usually bacteria, that invade the udder, multiply in the milk producing tissues, and synthesize toxins, a by-product of bacterial metabolism. The characteristic features of inflammation are swelling, heat, redness, pain and disturbed function.

While the animal immune system can fight intramammary infections, many chronic infections remain sub-clinical (asymptomatic) and undetected unless diagnosed by laboratory testing. Sub-clinical mastitis can result in a reservoir of microorganisms, which can lead to the infection of other animals within the herd. More than 80 species of microorganisms have been identified as causal agents, although approximately 95% of mastitis is caused by four pathogens: *Staphylococcus aureus*, *Streptococcus agalactiae*, *Streptococcus dysagalactiae*, and *Streptococcus uberis*. Mastitis causing pathogens fall into two categories namely contagious and environmental. Contagious bacteria, such as *Streptococcus agalactiae* and *Staphylococcus aureus*, primarily colonize host tissue sites such as mammary glands, teat canals, teat skin lesions etc. and are spread from one infected cow to another during the milking process. Environmental bacteria, often streptococci, enterocci and coliform organisms, are commonly present within the cow's surroundings from sources such as cow feces, soil, plant material, bedding or water, and infect by casual opportunistic contact with an animal. This distinction, although not exclusive, is of practical importance because different dairy herd maintenance measures are needed for the different groups of microorganisms. In all bovine mastitis cases, whatever the causal microorganism, the route of transmission of the invading pathogen into the inner gland of the udder is through the teat orifice and teat canal.

Management of dairy herds focuses attention on treatment of both established mastitis and on prevention of new intramammary infections. Therapy and hygiene are two fundamental components of an effective mastitis control program. Each is applied in concert, and each operates independently. The primary effect of therapy is to eliminate established infections, whereas, hygiene reduces the incidence of new infection by interrupting transmission vectors. A non-exhaustive list of ancillary factors which may be employed for the elimination and prevention of mastitis, include, post-lactation antibiotic infusion into the udder (e.g., dry cow treatment); and, post-milking teat antisepsis or "teat dipping" during lactation.

Researchers agree, and an abundance of published evidence supports the concept, that dipping teats into an effective antimicrobial solution immediately after each milking is the single most effective procedure for decreasing new intramammary infections in lactating cows. Between 1955 to 1970, Dodd and co-workers conducted extensive epidemiologic investigations in commercial dairy herds (F. K. Neave, F. H. Dodd, and R. G. Kingwell, 1966, "A Method of Controlling Udder Disease", Vet. Rec. 78:521; F. K. Neave, F. H. Dodd, R. G. Kingwell and D. R. Westgarth, 1969, "Control of Mastitis in the Dairy Herd by Hygiene and Management", J. Dairy Sci. 52:696; F. H. Dodd, D. R. Westgarth, F. K. Neave and R. G. Kingwill, 1969, "Mastitis—The Strategy of Control", J. Dairy Sci. 52:689; and F. H. Dodd, and F. K. Neave, 1970, "Mastitis Control", Proceedings, Nat'l. Inst. Res. Dairying, pp. 21–60). From this work, they developed the conceptual basis for modern mastitis control methods of which teat dipping is an integral component. The efficacy and value of teat dipping has since been confirmed in dozens of field trials, and it is now accepted that an effective teat dip can reduce the incidence of new intramammary infections at least 50% and often up to 90%.

To reduce mastitis, commercial teat dips have been developed containing a variety of antimicrobial agents including iodophors, quaternary ammonium compounds, chlorhexidine salts, chlorine release compounds (e.g. alkali hypochlorites), oxidizing compounds (e.g. hydrogen peroxide, peracids), protonated carboxylic acids (e.g. octanoic, nonanoic, decanoic, acids), acid anionics (e.g. alkylaryl sulfonic acids), and chlorine dioxide (from chlorite). These agents, which have varying degrees of effectiveness, limit the transmission of mastitis by reducing pathogen populations on the teat. Teat dips, can also be divided into two broad classifications. The Class I type are antimicrobial and are applied to kill microorganisms already present in the teat canal or on the surface of the teat skin By design, their microbiological effect is immediate and they primarily target the contagious organisms that are vectored between animals during the pre-milking, milking and post-milking process. The Class II type teat dip, often referred to as a "teat sealer," is a film-forming or coating composition which may or may not be antimicrobial; and, functions by developing a residual protective barrier on the teat thus providing prophylaxis by sealing the teat orifice from environmental contamination. The film, which forms on the surface of the teat, serves as a physical barrier through which mastitis causing pathogens cannot penetrate during the intermilking period.

General disclosures of teat dip technology are shown in, for example, "Current Concepts of Bovine Mastitis." 1996, Fourth Ed. National Mastitis Council, Madison Wis.; P. A. Murdough and J. W. Pankey, 1993. "Evaluation of 57 Teat Sanitizers Using Excised Cow Teats", J. Dairy Sci. 76:2033–2038; J. W. Pankey et al., 1984, "Uptake on Post-milking Teat Antiseptics", J. Dairy Sci. 67:1336–1353; R. J. Farnsworth, 1980, "Role of Teat Dips in Mastitis Control", J. Am. Vet. Med. Assoc. 76:1116–1118; W. N.

Philpot, 1979, "Control of Mastitis by Hygiene and Therapy", J. Dairy Sci. 62:168–176; W. N. Philpot and J. W. Pankey, 1978, "Hygiene in the Prevention of Udder Infections V. Efficacy of Teat Dips Under Experimental Exposure to Mastitis Pathogens", J. Dairy Sci. 61:956–963; R. P. Natzke, 1977, "Role of Teat Dips and Hygiene is Mastitis Control", J. Amer. Vet. Med. Assoc. 170:1196–1198; W. N. Philpot and J. W. Pankey, 1975, "Hygiene in the Prevention of Udder Infections. III. Effectiveness of 59 Teat Dips for Reducing Bacterial Populations on Teat Skin", J. Dairy Sci. 58:209–216; R. J. Eberhart and J. M. Buckalew, 1972, "Evaluation of a Hygiene and Dry Period Therapy Program for Mastitis Control", J. Dairy Sci. 55:1683–1691; W. D. Schultze and J. W. Smith, 1972, "Effectiveness of Postmilking Teat Dips", J. Dairy Sci. 55:426–431; D. P. Wesen and L. H. Schultz, 1970, "Effectiveness of a Post-Milking Teat Dip in Preventing New Udder Infections", J. Dairy Sci. 53:1391–1403; and British Pat. No. 1,144,637 (Kelco Chemicals Ltd.), published Mar. 5, 1969.

Typical disclosures of intermilking or protective (barrier-type) film-forming teat dips or teat "sealers" can be found in Akers et. al., U.S. Pat. No. 3,066,071, issued Nov. 27, 1962; Kraus, U.S. Pat. No. 3,222,252, issued Dec. 7, 1965 (but, see Philpot et. al., J. Dairy Science 58:205–216); Coughman and Brown, U.S. Pat. No. 3,993,777, issued Nov. 23, 1976; Pugliese, U.S. Pat. No. 4,049,830, issued Sep. 20, 1977; and Andrews et al., U.S. Pat. No. 4,113,854, issued Sep. 12, 1978. One disadvantage of many such film-forming agents is their tendency to form a "hard" film, which is tenacious and often difficult to remove.

There is a growing acceptance among academics, veterinarians and dairy herd management that proactive maintenance of teat health and skin condition is an integral part of a complete program for the prevention, control and remedial correction of mastitis in mild producing animals. A growing number of publications support this (see for example, M. D. McKinzie and T. C. Hemling, 1995, "The Effect of Teat Skin Condition on Milk Yield and Milkout Time", National Mastitis Council Proceedings, pp 160–163; L. K. Fox, 1992, "Colonization of Staphylococcus Aureus On Chapped Skin: Effect of Iodine and Chlorhexidine Postmilking Teat Disinfectants", J. Dairy Sci. 75:66; and J J Goldbert et al., 1994, "Evaluation of Teat Conditioning Qualities of Postmilking Teat Dips", National Mastitis Council technology transfer Session, Orlando, Fla. The assertion is that a healthy milk delivery organ can naturally retard and more readily withstand the adverse affects of infection.

Although many teat dip products are available, and there remains a continuing need for new and effective teat dip compositions having immediate and long lasting antimicrobial effect against a wide spectrum of mastitis causing organisms; there is need for such antimicrobial compositions which additionally provide superior skin conditioning and health maintenance functions.

Additionally, many teat dip products are not conducive for use in cold environment conditions. For example, many teat dip compositions include a large amount of water, and can freeze in cold environments. Such compositions can freeze on the teats, and cause irritation, chapping and frostbite, and such conditions can enhance the incidence of mastitis caused by opportunistic invasive microorganisms.

Thus, although many teat dip products are available, there is a continuing need for new and effective teat dip compositions having immediate and long lasting antimicrobial effect against a wide spectrum of mastitis causing organisms that are formulated for use in cold environments.

SUMMARY OF THE INVENTION

The present invention is directed to novel antimicrobial compositions, which can be used as a teat dip for milk producing animals. At least some embodiments of this invention provide both superior antimicrobial protection against mastitis causing organisms and skin conditioning for maintenance of healthy teats; and in addition provide protection against the adverse affects of frigid weather, one of the major causes of irritation, chapping and frostbite, which enhance the incidence of mastitis caused by opportunistic invasive microorganisms. Still further benefit is accomplished by application of at least some preferred compositions of this invention on teats which are already in poor health condition, for example by application on so-termed "hospital pen animals", to facilitate faster repair and the healing process.

It will be noted that at several places throughout the Specification, guidance is provided through lists of examples. In each instance, the recited lists serve only as representative groups. It is not meant, however, that the lists are exclusive.

In general, an antimicrobial composition of the invention comprises, a $C_6$-$C_{12}$ fatty acid and a carrier medium including a freezing point depressant component. In preferred embodiments, the fatty acid can be a $C_7$-$C_9$ fatty acid. A particularly preferred fatty acid is heptanoic acid. In some preferred embodiments, the freezing point depressant component makes up greater than 60% by wt. of the composition. Particularly preferred freezing point depressant components are selected from the group consisting of propylene glycol, glycerine, and mixtures thereof.

In preferred embodiments of a teat dip composition, the teat dip formulation also includes significantly high concentration of one or more occlusive agents which provide a protective barrier on the teat surface against irritating physical abrasion as from the mechanical action of the milking equipment or tissue damaging or disruptive environmental conditions such as frigid temperatures, wind chill, dehydration, windburn and sunburn. These agents may be, as example, but not meant to be inclusive: surfactants, emollients, lubricants, humectants, moisturizers, solvents etc. or mixtures thereof having the purpose of generally protecting and conditioning the teat skin surfaces thereby promoting healthy milk producing animals. In some preferred embodiments, some of the freezing point depressant components have a dual function as a occlusive agent as well as a freezing point depressant component.

A teat dip composition can also include a rheology modifier, a film-forming agent or admixture, a buffer system, a hydrotope or coupler, or solvent, an emollient, skin conditioner or a lubricant, surfactant, color marker, fragrance, anti-irritants and healing agents, antioxidants, UV absorbers, vitamins or admixtures thereof.

In general, the invention also includes a method of controlling mastitis in milk producing animals comprising applying the composition to a teat of an animal. The composition of the invention is particularly beneficial when applied in colder environmental temperatures, for example in temperatures of below 40° F.

DETAILED DESCRIPTION OF THE INVENTION

The present invention is directed to antimicrobial compositions. In general, the compositions include a fatty acid, typically a $C_6$-$C_{12}$ fatty acid and a carrier medium including a freezing point depressant component. As used herein, "freezing point depressant component" means a constituent or mixture of constituents within the composition that act to reduce the freezing point of the composition below that of the composition without that constituent. Typically, the freezing point depressant component acts to reduce the freezing point of the composition below the freezing point of water. The compositions of the invention can be advantageously used as a teat dip for control of mastitis in milk producing animals. The compositions of the invention are formulated for use in cold temperature environments, for example in environments having a temperature of 40° F. or below. However, formulating of the invention can also be used in warm environment conditions. Some embodiments are particularly useful to facilitate faster repair of teats that are already in poor health regardless of the temperature. For example, some embodiments are particularly beneficial on chapped or irritated teats.

Components Used in a Teat Dip Embodiment of the Invention

The compositions of the invention can be formulated as a teat dip for mastitis prevention or control. According to this embodiment, the compositions can comprise a carboxylic acid, such as a fatty acid in a carrier medium comprising a freezing point depressant component. Preferably, the fatty acid comprises in the range of 0.01 to 5% by wt. of the total composition, and the freezing point depressant component comprises greater than 60% by wt. of the total composition.

Teat dip compositions may optionally also include, a rheology modifier or admixture, a film-forming agent or admixture, a buffer system, a hydrotrope, a coupler or admixtures thereof, a surfactant or surfactant admixture, an emollient, a skin-conditioner or a lubricant or admixtures thereof, one or more adjuvants, etc. The preferred compositions of the invention comprise ingredients, which are generally regarded as safe, and are not of themselves or in admixture incompatible with milk or milk by-products. Ingredients may also be selected which are cooperative in their combined effects whether incorporated for physical integrity of the formulations or to facilitate healing and overall health of the teat. The carrier functions to dilute the active ingredients and facilitate application to the intended surface.

The compositions of the invention can be provided as a ready-to-use formulation or as concentrates, which are diluted prior to use. Hence, throughout this disclosure, reference will be made to "working compositions" which are the compositions, which are actually used as a teat dip. Thus, a working composition includes, for example, ready-to-use compositions as well as concentrates, which have been diluted for use in a particular application. Methods for preparing concentrates based on the disclosure herein of working compositions are within the knowledge of one of skill in the art.

In preferred embodiments, a teat dip composition of the invention provides a protective soft barrier over the teat. A "soft barrier" provides a self annealing barrier which can flow to re-cover areas of the teat from which the dip may have been removed when the animal lays down, walks through the pasture or is subject to some other event which causes inadvertent removal of the dip. Advantageously, however, a herein disclosed soft barrier can also be readily removed from the teat using routine washing procedures prior to milking without congealing, pilling or leaving some other undesired residue on the teat. The soft barrier is provided and rheology modifiers described further below.

Thus, unlike prior film-forming barriers, the protective soft barrier provided herein is a soft, non-peeling barrier that can undergo plastic deformation, for self-repair, without breaking or cracking.

Carrier Medium Including Freezing Point Depressant Component

The carrier medium of a composition of the invention can generally be an aqueous medium such as water, or an organic liquid such as an oil, a surfactant, an alcohol or polyol, an ester, an ether, or an organic or aqueous mixture of any of these. The carrier medium includes high concentrations of non-aqueous, preferably water miscible liquids or soluble solids that act as a freezing point depressant component for the composition. Preferred freezing point depressant components also have some degree of skin conditioning properties, and provide protection against the adverse affects of frigid weather. Examples of preferred freezing point depressant components include polyols, and mixtures thereof. Preferred polyols include propylene glycol; glycerin; sorbitol; and homologs, homopolymers and derivatives thereof and mixtures thereof. In an embodiment, the freezing point depressant component is a mixture of propylene glycol and glycerin. Preferably, the freezing point depressant component of the carrier medium make up greater than 60%, in some embodiments, greater than 65%, in some other embodiments, greater than 70%, and in yet other embodiments, greater than 75% by weight of the total composition.

The freezing point depressant components within the composition have the desired effect of reducing the freezing point of the composition below that of water. In some embodiments, the freezing point of the composition is below 25° F., in some embodiments, below 15° F., in some embodiments, below 10° F., in some embodiments below 0° F., in some embodiments below −10° F., and in yet other embodiments, below −20° F. By providing the composition with a low freezing point, the freezing point depressants allow the composition to be used in cold temperature environments, and help to prevent chapping, irritation, windburn, frostbite, and other such conditions on the teats of an animal associated with cold environments. Further, the compositions are less likely to freeze and can be applied in colder temperatures that many teat dips.

Fatty Acid

The compositions of the invention also include a carboxylic fatty acid component, which provides the antimicrobial activity. For optimal antimicrobial activity, the pH of the composition is preferably at or below the pKa of the fatty acid. Thus, in preferred compositions, the relationship of pH to pKa provides antimicrobial activity through carboxylic fatty acids, which are substantially protonated. Preferred compositions of the invention have a pH in the range of about 3.5 to about 6.0, typically about 4.0 to about 5.0 and, in one preferred embodiment, about 4.5. Although a wider range of pH is possible, typically, below pH 3.5 undesirable skin irritation may occur and above pH 6.0 dissociation or conversion to the ionized form may reduce the antimicrobial efficacy of the fatty acid.

Fatty acids suitable for a composition of the present invention include $C_6$-$C_{12}$ fatty acids. Preferred fatty acids have a chain length from about $C_7$-$C_9$. One particularly preferred fatty acid is heptanoic acid that has seven carbon atoms, including the carboxyl group, and has a pKa of 4.4. In addition to its preferred water solubility, heptanoic acid is not significantly irritating to the tissues. In an embodiment, the antimicrobial component consists essentially of heptanoic acid.

In general, the fatty acid component of the invention can be present at about 0.01% to about 5.0% of the total weight of the working composition. For example, when heptanoic acid is the fatty acid, it may be present at about 0.01% to about 5% of the total weight of the working composition. In a working composition having a pH of about 4.5, heptanoic acid may be present at about 0.1% to about 5% of the total working solution, preferably at about 0.5% to about 2.0%.

The antimicrobial components of the composition can be mixed in the carrier medium and include buffers, surface active agents and/or couplers to provide a pH and solubility suitable for efficient bactericidal effect with low or no irritation to the tissues of the teat. The buffer system is present to prevent the likelihood of pH drift under typical use conditions. In general, the buffer system can include any weak acid and its conjugate base. Preferred bases used to adjust the pH of the compositions include hydroxides of the alkaline earth metals, for example NaOH, KOH, LiOH, etc.

Maintenance of the pH of compositions described in this invention is preferred to minimize undesirable chemical changes, which may inhibit the microbiological efficacy of the antimicrobial components or cause toxic or irritating effect upon the teat. Any compatible organic or inorganic material or mixture of materials which has the desired effect of maintaining the composition pH within prescribed ranges can be utilized as the buffering agent or system in the invention. Factors which may cause undesirable pH shifts include the presence of naturally occurring chemicals brought into the composition, after application onto the teat, by skin exudations, milk or environmental soils; and, pH drifting which sometimes accompanies chemical equilibriums established within compositions as ingredients are changed or concentrations varied, for example, concentration changes which can occur as a teat dip dries on the teat.

In general, the pH of bovine mastitis control treatments can vary from a low of about pH 2.5 to a maximum of approximately 10.5 depending primarily upon the choice of antimicrobial agent being incorporated in the composition. Therefore the buffering agent or system is chosen accordingly. Most common commercially-available weak inorganic and organic acids can be used in the invention. Preferred weak inorganic acids include phosphoric acid and sulfamic acid. Useful weak organic acids include acetic acid, hydroxyacetic acid, citric acid, tartaric acid, lactic acid, glycolic acid, adipic acid, succinic acid, propionic acid, malic acid, alkane sulfonic acids, cycloalkane sulfonic acids, etc. Mixtures of organic and inorganic acids can also be used. One typical and preferred buffer system is citric acid and its alkali metal salt.

Solubilizing agents called hydrotropes or couplers or solvents may be generally used in compositions of the invention to maintain physical single-phase integrity and storage stability. To this end, any number of ingredients known to those skilled in the formulation art may be employed, such as monofunctional and polyfunctional alcohols. These preferably contain from about 1 to about 6 carbon atoms and from 1 to about 6 hydroxy groups. Examples include ethanol, isopropanol, n-propanol, 1, 2-propanediol, 1, 2-butanediol, 2-methyl-2, 4-pentanediol, mannitol and glucose. Also useful are the higher glycols, polyglycols, polyoxides, glycol ethers and propylene glycol ethers. Additional useful hydrotropes include the free acids and alkali metal salts of sulfonated alkylaryls such as toluene, xylene, cumene and phenol or phenol ether or diphenyl ether sulfonates; alkyl and dialkyl naphthalene sulfonates and alkoxylated derivatives.

Additional Components

A composition of the invention may also contain one or more rheology modifiers, to enhance viscosity, or thicken the composition to facilitate adherence of a dip to the teat. Adherence enables the composition to remain in contact with transient and resident pathogenic bacteria for longer periods of time, promoting microbiological efficacy and resisting waste because of excessive dripping. The rheology modifier may be a film former or act cooperatively with a film-forming agent to form a barrier that provides additional protection. However, in preferred embodiments, a teat dip composition of the invention provides a soft barrier, rather than a well-defined film.

Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SILS®) which have been fumed or precipitated to create particles with large surface to size ratios. Suitable natural hydrogel thickeners are primarily vegetable derived exudates. For example, tragacanth, karaya, and acacia gums; and extractives such as carrageenan, locust bean gum, guar gum and pectin; or, pure culture fermentation products such as xanthan gum. Chemically, all of these materials are salts of complex anionic polysaccharides. Synthetic natural-based thickeners having application are cellulose derivatives wherein the free hydroxyl groups on the linear anhydro-glucose polymers have been etherified or esterified to give a family of substances, which dissolve in water and give viscous solutions. This group of materials includes the alkyl and hydroxylalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

A preferred rheology modifier is polyvinylpyrrolidone, K-90 manufactured by International Specialty Products. This rheology modifier is particularly advantageous in that it is very water soluble, compatible in compositions containing high formula percentages of organic materials and is believed to retard skin irritation.

Suitable surfactants or surfactant admixtures can be selected from compatible water-soluble or water dispersible nonionic, or anionic surface-active agents; or mixtures of each or both types. Non-ionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Useful nonionic surfactants in the present invention include: Block polyoxypropylene-polyoxyethylene polymeric compounds based upon propylene glycol, ethylene glycol, glycerol and trimethylolpropane as the initiator reactive hydrogen compound. Examples of polymeric compounds made from a sequential propoxylation and ethoxylation of initiator are commercially available under the trade name PLURONIC® manufactured by BASF Corp. PLURONIC® compounds are difunctional (two reactive hydrogens) compounds formed by condensing ethylene oxide with a hydrophobic base formed by the addition of propylene oxide to two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule.

Likewise useful nonionic surfactants include condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade name NEODOL® manufactured by Shell Chemical Co. and ALFONIC® manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above delineated carbon atoms range or it can consist of an acid having a specific number of carbon atoms within the range. Examples of commercial compounds of this chemistry are available on the market under the trade name NOPALCOL® manufactured by Henkel Corporation and LIPOPEG® manufactured by Lipo Chemicals, Inc. In addition to ethoxylated carboxylic acids, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

Also useful nonionic surfactants include the condensation products of one mole of alkyl phenol wherein the alkyl constituent contains from about 8 to about 18 carbon atoms with from about 3 to about 50 moles of ethylene oxide. The alkyl group can, for example, be represented by diisobutylene, di-amyl, polymerized propylene, isoctyl, nonyl, and di-nonyl. Examples of commercial compounds of this chemistry are available on the market under the trade name IGEPAL® manufactured by Rhone-Poulenc and TRITON® manufactured by Union Carbide. The surfactants used in the present compositions are also selected to improve solubility for removal of the composition from the teat prior to milking.

Teat dip compositions of the present invention can also include an emollient, moisturizer, humectant or re-fatting agent to lubricate, condition and generally reduce irritation and promote the healing of the teat surface of which may result either from the antimicrobial component, from the mechanical action of the milking machine or from environmental conditions such as frigid temperatures wind chill, dehydration, abrasion, windburn and sunburn. Any water miscible, soluble or dispersible skin-conditioning agent may be used in this invention. Compositions such as polyhydric alcohols are useful in the invention including glycerin, sorbitol, mannitol, and propylene glycol and its homopolymers; fatty acid esters of simple monohydril alcohols including isopropyl palmitate or isopropyl myristate and similar esters; polyol esters of fatty acids; and, ethoxylated lanolins, vegetable oils, and similar natural sourced derivatives such as aloe. Preferred emollients to be used in the invention include glycerin, and propylene glycol and lanolin. It should be noted that preferably the freezing point depressant component in the carrier medium also act as emollient/moisturizer/humectants. For example, in some preferable embodiments, propylene glycol and glycerin are present in high concentrations in the composition, and act as both freezing point depressants and emollients.

The compositions of the invention may also optionally include medicaments, for example sunscreens such as paraamino benzoic acid and healing agents such as allantoin or tocopheryl acetate or α-hydroxy carboxylic acids or urea to provide curative action and stimulation of formation of new tissue; preservatives such as methyl paraben, propyl paraben, sorbic and benzoic acids or salts thereof to retard bacterial growth and prolong shelf life; antioxidants such as BHT (butylated hydroxytoluene), BHA (butylated hydroxyanisole), TBHQ (tert-butylhydroquinone), or propyl gallate to retard oxidative or hydrolytic degradation; sequestering agents such as aminopolyacetates, polyphosphonates, aminopolyphosphonates, polycarboxylates, and condensed phosphates; dispersants or suspending agents having polyelectrolytic character such as polyacrylate and similar polycarboxylates of homopolymeric or copolymeric structure; and manufacturing processing agents, for example defoam additives employed to facilitate blending and mixing.

The compositions can also include, dyes, pigments, marking agents, or other such components, as is generally known.

Preferred Methods of Using the Compositions

The compositions of the invention are useful in a method for controlling mastitis in milk producing animals. Generally, the method includes applying an antimicrobial composition embodying the invention a teat of an animal. Due to the freezing point depressant component within the composition, the compositions of the invention are particularly useful for methods wherein the antimicrobial composition is applied in environmental temperatures of below 40° F. or is applied to the teat of an animal that will be exposed to environmental temperatures of below 40° F. within 12 hours of the application. In some embodiments of such methods, the environmental temperatures can be below 30° F., below 20° F., or below 10° F.

Although the compositions of the invention are generally formulated for use in colder environmental temperatures, as discussed above, at least some embodiments of the compositions can be used in methods of treating teats on a milk producing animal which are already in poor health condition, for example by application on so-termed "hospital pen animals", to facilitate faster repair and the healing process.

The following examples are provided to further describe certain advantageous compositions according to the invention. The Examples, however, are not intended to limit the scope of the compositions within the spirit and scope of the invention.

EXAMPLES

Example 1

Formulation of Teat Dip Composition

The present Example provides one procedure for preparing a working composition of a teat dip composition according to one embodiment of the invention. This procedure can be used regardless of the total weight of the composition formulated. Thus, while a particular weight percentage of a component may vary among formulations, the procedure used for mixing the components is the same. It will be appreciated that other procedures can be used and are within the knowledge of one skilled in the art.

Deionized water is added to a stainless steel tank having a variable speed pitched blade turbine. The tank is agitated and the surfactant, sodium dioctylsulfosuccinate, is then added, with about 15 minutes of mixing and allowed to solubilize the surfactant. Polyvinylpyrrolidone K-90 is charged and mixed until completely solubilized. Preferably, the Polyvinylpyrrolidone is completely solubilized prior to addition of subsequent components.

Propylene glycol (technical), glycerin (e.g., 96% USP), ethoxylated lanolin, the fatty acid (e.g., heptanoic acid) and the fragrance, methyl solicylate are added and mixed for about 15 minutes to incorporate them into the mixture. A buffer, such as anhydrous granular citric acid is slowly added to the mixture and mixed until solubilized. Liquid 45% potassium hydroxide and blue dye are then added and the entire formula blended until the mixture appearance is uniform.

The preferred pH for a teat dip composition is about 3.5 to about 6. If the pH is less than the preferred range, a base such as potassium hydroxide can be added incrementally until the appropriate pH is achieved. If the pH is greater than the preferred range, an acid such as phosphoric acid can be added incrementally until the appropriate pH is obtained.

Tables 1–7 provide exemplary formulations for some teat dip compositions according to the invention.

TABLE 1

Teat Dip Formulation 1

| ITEM | RAW MATERIAL | RM CODES | WT % |
|---|---|---|---|
| 1 | DI Water | 100032 | 18.776 |
| 2 | Sodium Dioctylsulfosuccinate, (AEROSOL OT-100) - Dioctylsulfosuccinate | 171000 | 0.020 |
| 3 | Polyvinylpyrrolidone (Tradename PVP K-90) | 230076 | 0.500 |
| 4 | Propylene Glycol, Technical | 164079 | 63.000 |
| 5 | Glycerine, 96% USP | 164186 | 15.000 |
| 6 | Ethoxylated Lanolin, 75 EO., (Laneto 50) | 172002 | 0.100 |
| 7 | Heptanoic Acid | 190454 | 1.750 |
| 8 | Methyl Salicylate | 261016 | 0.050 |
| 9 | Citric Acid, Anhyd., Technical | 124032 | 0.500 |
| 10 | Potassium Hydroxide, 45% Liquid | 114041 | 0.289 |
| 11 | FD & C Blue #1 (Food Blue#2) | 271411 | 0.015 |
| | | | 100.000 |

Polyvinylpyrrrolidone(PVP K90): International Specialty Products, Wayne, N.J.
Aerosol OT: Cytec Industries, Inc., West Paterson, N.J.
Laneto 50: R.I.T.A. Corp., Woodstock, IL.

TABLE 2

Teat Dip Formulations 2–9

| ITEM | RAW MATERIAL | RM CODES | 2 WT % | 3 WT % | 4 WT % | 5 WT % | 6 WT % | 7 WT % | 8 WT % | 9 WT % |
|---|---|---|---|---|---|---|---|---|---|---|
| 1 | DI Water | 100032 | 22.650 | 22.503 | 23.347 | 22.498 | 23.347 | 23.350 | 23.355 | 23.400 |
| 2 | Neodol 25-9 | 173534 | 0.100 | 0.100 | 0.100 | | | | | |
| 3 | AEROSOL OT | 171000 | | | | 0.100 | 0.100 | 0.100 | 0.100 | 0.100 |
| 4 | Propylene Glycol | 164079 | 75.000 | 75.000 | 75.000 | 75.000 | 75.000 | 75.000 | 75.000 | 75.000 |
| 5 | Heptanoic Acid, C-7 | 190454 | 1.500 | 1.500 | 1.500 | 1.500 | 1.500 | 1.500 | 1.500 | 1.500 |
| 6 | Lactic Acid, 88% | 810432 | 0.750 | 0.897 | | 0.902 | | | | |
| 7 | Phosphoric Acid, 75% | 121012 | | | 0.053 | | 0.053 | 0.050 | 0.045 | |
| | Total | | 100.000 | 100.000 | 100.000 | 100.000 | 100.000 | 100.000 | 100.000 | 100.000 |

Neodol 25-9: Shell Chemical Co., Houston, TX.

TABLE 3

Teat Dip Formulations 10–17

| ITEM | RAW MATERIAL | RM CODES | 10 WT % | 11 WT % | 12 WT % | 13 WT % | 14 WT % | 15 WT % | 16 WT % | 17 WT % |
|---|---|---|---|---|---|---|---|---|---|---|
| 1 | DI Water | 100032 | 23.393 | 23.375 | 23.325 | 23.313 | 23.307 | 20.340 | 23.250 | 20.350 |
| 2 | Neodol 25-9 | 173534 | | | | | | | | |
| 3 | AEROSOL OT | 171000 | 0.100 | 0.100 | 0.100 | 0.100 | 0.100 | 0.020 | 0.100 | 0.100 |
| 4 | PVP K-90 | 230076 | | | | | | | 0.100 | |
| 5 | Rheothik 80-11, 16% | | | | | | | | | 3.000 |
| 6 | Propylene Glycol | 164079 | 75.000 | 75.000 | 75.000 | 75.000 | 75.000 | 73.000 | 75.000 | 75.000 |
| 7 | Glycerine, 96% | 164186 | | | | | | 5.000 | | |
| 8 | Laneto 50 | 810762 | | | | | | 0.100 | | |
| 9 | Heptanoic Acid, C-7 | 190454 | 1.500 | 1.500 | 1.500 | 1.500 | 1.500 | 1.500 | 1.500 | 1.500 |
| 10 | Phosphoric Acid, 75% | 121012 | | | | 0.045 | 0.048 | 0.040 | 0.050 | 0.050 |
| 11 | KOH, 45% | 114041 | 0.007 | 0.025 | 0.075 | | | | | |
| 12 | FD&C Yellow #6 | 810739 | | | | 0.042 | 0.045 | | | |
| | Total | | 100.000 | 100.000 | 100.000 | 100.000 | 100.000 | 100.000 | 100.000 | 100.000 |

Rheothick 80-11: Henkel Corp, Chemicals Group Care Chemicals, Ambler, PA

TABLE 4

Teat Dip Formulations 18–25

| ITEM | RAW MATERIAL | RM CODES | 18 WT % | 19 WT % | 20 WT % | 21 WT % | 22 WT % | 23 WT % | 24 WT % | 25 WT % |
|---|---|---|---|---|---|---|---|---|---|---|
| 1 | DI Water | 100032 | 19.553 | 19.503 | 19.503 | 19.453 | 19.513 | 19.463 | 19.463 | 19.517 |
| 2 | AEROSOL OT | 171000 | 0.020 | 0.020 | 0.020 | 0.020 | 0.020 | 0.020 | 0.020 | 0.020 |
| 3 | Rheothik 80-11, 16% | | 0.750 | 0.750 | 0.750 | 0.750 | 0.750 | 0.750 | 0.750 | 0.750 |
| 4 | Propylene Glycol | 164079 | 73.000 | 73.000 | 73.000 | 73.000 | 73.000 | 73.000 | 73.000 | 73.000 |
| 5 | Glycerine, 96% | 164186 | 5.000 | 5.000 | 5.000 | 5.000 | 5.000 | 5.000 | 5.000 | 5.000 |
| 6 | Laneto 50 | 810762 | 0.100 | 0.100 | 0.100 | 0.100 | 0.100 | 0.100 | 0.100 | 0.100 |
| 7 | Heptanoic Acid, C-7 | 190454 | 1.500 | 1.500 | 1.500 | 1.500 | 1.500 | 1.500 | 1.500 | 1.500 |
| 8 | KOH, 45% | 114041 | 0.077 | 0.077 | 0.077 | 0.077 | 0.077 | 0.077 | 0.077 | 0.077 |
| 9 | Benzaldehyde | 283028 | | 0.050 | | | | 0.050 | | 0.030 |
| 10 | Vanillin | 260607 | | | 0.050 | 0.100 | | | 0.050 | |
| 11 | FD&C Blue #1 | 810184 | | | | | 0.010 | 0.010 | 0.010 | 0.006 |
| 12 | FD&C Red #3 | 274449 | | | | | 0.030 | 0.030 | 0.030 | |
| | Total | | 100.000 | 100.000 | 100.000 | 100.000 | 100.000 | 100.000 | 100.000 | 100.000 |

TABLE 5

Teat Dip Formulations 26–33

| ITEM | RAW MATERIAL | RM CODES | 26 WT % | 27 WT % | 28 WT % | 29 WT % | 30 WT % | 31 WT % | 32 WT % | 33 WT % |
|---|---|---|---|---|---|---|---|---|---|---|
| 1 | DI Water | 100032 | 20.118 | 20.099 | 20.160 | 19.179 | 19.133 | 19.152 | 19.194 | 19.312 |
| 2 | AEROSOL OT | 171000 | 0.020 | 0.020 | 0.020 | 0.020 | 0.020 | 0.020 | 0.020 | 0.020 |
| 3 | KLUCEL HF | 230151 | 0.100 | 0.100 | 0.100 | | | | | |
| 4 | PVP K-90 | 230076 | | | | 1.000 | 1.000 | 1.000 | 1.000 | 1.000 |
| 6 | Propylene Glycol | 164079 | 73.000 | 73.000 | 73.000 | 73.132 | 73.132 | 73.132 | 73.132 | 73.000 |
| 7 | Glycerine, 96% | 164186 | 5.000 | 5.000 | 5.000 | 5.000 | 5.000 | 5.000 | 5.000 | 5.000 |
| 8 | Laneto 50 | 810762 | 0.100 | 0.100 | 0.100 | 0.100 | 0.100 | 0.100 | 0.100 | 0.100 |
| 9 | Heptanoic Acid, C-7 | 190454 | 1.500 | 1.500 | 1.500 | 1.500 | 1.500 | 1.500 | 1.500 | 1.500 |
| 10 | Phosphoric Acid, 75% | 121012 | 0.012 | 0.012 | 0.012 | | | | | |
| 11 | KOH, 45% | 114041 | 0.008 | 0.008 | 0.008 | 0.004 | 0.004 | 0.004 | 0.004 | 0.003 |
| 12 | Benzaldehyde | 283028 | | | | 0.050 | 0.050 | 0.050 | 0.050 | |
| 13 | Vanillin | 260607 | 0.100 | 0.100 | 0.100 | | | | | |
| 14 | Methyl Salicylate | 261016 | | | | | | | | 0.050 |
| 15 | FD&C Yellow #5 | 271684 | 0.002 | 0.060 | | | 0.060 | 0.002 | | |
| 16 | FD&C Blue #1 | 810184 | | 0.001 | | 0.015 | 0.001 | | | 0.015 |
| 17 | FD&C Red #3 | 274449 | 0.040 | | | | | 0.040 | | |
| | Total | | 100.000 | 100.000 | 100.000 | 100.000 | 100.000 | 100.000 | 100.000 | 100.000 |

TABLE 6

Teat Dip Formulations 34–41

| ITEM | RAW MATERIAL | RM CODES | 34 WT % | 35 WT % | 36 WT % | 37 WT % | 38 WT % | 39 WT % | 40 WT % | 41 WT % |
|---|---|---|---|---|---|---|---|---|---|---|
| 1 | DI Water | 100032 | 19.267 | 19.306 | 19.283 | 20.161 | 19.309 | 20.207 | 19.335 | 18.695 |
| 2 | AEROSOL OT | 171000 | 0.020 | 0.020 | 0.020 | | 0.020 | 0.020 | | 0.020 |
| 3 | KLUCEL HF | 230151 | | | | 0.100 | | 0.100 | | |
| 4 | PVP K-90 | 230076 | 1.000 | 1.000 | 1.000 | | 1.000 | | 1.000 | 1.000 |
| 5 | Propylene Glycol | 164079 | 73.000 | 73.000 | 73.000 | 73.000 | 63.000 | 63.000 | 63.000 | 63.000 |
| 6 | Glycerine, 96% | 164186 | 5.000 | 5.000 | 5.000 | 5.000 | 15.000 | 15.000 | 15.000 | 15.000 |
| 7 | Laneto 50 | 810762 | 0.100 | 0.100 | 0.100 | 0.100 | 0.100 | 0.100 | 0.100 | 0.100 |
| 8 | Heptanoic Acid, C-7 | 190454 | 1.500 | 1.500 | 1.500 | 1.500 | 1.500 | 1.500 | 1.500 | 1.500 |
| 9 | KOH, 45% | 114041 | 0.003 | 0.003 | 0.003 | 0.008 | 0.006 | 0.008 | | 0.135 |
| 10 | Citric Acid, Anhyd. | 124032 | | | | | | | | 0.500 |
| 11 | Methyl Salicylate | 261016 | 0.050 | 0.050 | 0.050 | 0.050 | 0.050 | 0.050 | 0.050 | 0.050 |
| 12 | FD&C Yellow #5 | 271684 | 0.060 | 0.001 | | 0.060 | | | | |
| 13 | FD&C Yellow #6 | 810739 | | | 0.045 | | | | | |
| 14 | FD&C Blue #1 | 810184 | 0.001 | | | 0.001 | 0.015 | 0.015 | 0.015 | |
| 15 | FD&C Red #3 | 274449 | | 0.020 | | | | | | |
| | Total | | 100.000 | 100.000 | 100.000 | 100.000 | 100.000 | 100.000 | 100.000 | 100.000 |

Klucel HF: Hercules Inc., Aqualon Div., Wilmington, DE

TABLE 7

Teat Dip Formulations 42–47

| ITEM | RAW MATERIAL | RM CODES | 42 WT % | 43 WT % | 44 WT % | 45 WT % | 46 WT % | 47 WT % |
|---|---|---|---|---|---|---|---|---|
| 1 | DI Water | 100032 | 18.676 | 18.543 | 19.298 | 19.167 | 18.790 | 18.776 |
| 2 | AEROSOL OT | 171000 | 0.020 | 0.020 | 0.020 | 0.020 | 0.020 | 0.020 |
| 3 | PVP K-90 | 230076 | 1.000 | 1.000 | 0.499 | 0.500 | 0.500 | 0.500 |
| 4 | Propylene Glycol | 164079 | 63.000 | 63.000 | 62.897 | 63.000 | 63.000 | 63.000 |
| 5 | Glycerine, 96% | 164186 | 15.000 | 15.000 | 14.975 | 15.000 | 15.000 | 15.000 |
| 6 | Laneto 50 | 810762 | 0.100 | 0.100 | 0.100 | 0.100 | 0.100 | 0.100 |
| 7 | Heptanoic Acid, C-7 | 190454 | 1.500 | 1.500 | 1.498 | 1.500 | 1.750 | 1.750 |
| 8 | KOH, 45% | 114041 | 0.139 | 0.272 | 0.150 | 0.148 | 0.290 | 0.289 |
| 9 | Citric Acid, Anhyd. | 124032 | 0.500 | 0.500 | 0.499 | 0.500 | 0.500 | 0.500 |
| 10 | Methyl Salicylate | 261016 | 0.050 | 0.050 | 0.050 | 0.050 | 0.050 | 0.050 |
| 11 | FD&C Blue #1 | 810184 | 0.015 | 0.015 | 0.015 | 0.015 |  | 0.015 |
|  |  | Total | 100.000 | 100.000 | 100.000 | 100.000 | 100.000 | 100.000 |

Example 2

Sanitizing Efficacy of Teat Dip KX-6128 against Eight Mastitis Causing Organisms The objective of the analysis was to determine the sanitizing efficacy of the teat dip composition 1 (from Table 1 above) against *Staphylococcus aureus* ATCC 6538, *Escherichia coli* ATCC 11229, *Klebsiella pneumoniae* ATCC 4352, *Streptococcus agalactiae* ATCC 27056, *Streptococcus dysgalactiae* ATCC 27957, *Streptococcus uberis* ATCC 27958, *Enterobacter aerogenes* ATCC 13048, and *Pseudomonas aeruginosa* ATCC 15442 at a 15 second exposure time with a 10% milk challenge.

Test Method:

The method used in this example generally followed AOAC method 960.09, with the following deviations: the exposure contact time was reduced to 15 seconds from 30 seconds. Additionally, a 10% whole milk soil challenge was prepared by adding 10 mls of raw whole milk to 90 mls of test product and mixed, and from which 99 ml aliquot is used for the test (with 1 ml of specified inoculum).

Method Parameters:

| Test Substance Name | Concentration | mL of Test Substance | mL of Diluent |
|---|---|---|---|
| KX-6128 | 100% | 90 | 10 |

| Test Systems: | *Staphylococcus aureus* | ATCC 6538 |
|---|---|---|
|  | *Escherichia coli* | ATCC 11229 |
|  | *Klebsiella pneumoniae* | ATCC 4352 |
|  | *Enterobacter aerogenes* | ATCC 13048 |
|  | *Streptococcus agalactiae* | ATCC 27956 |
|  | *Streptococcus dysgalactiae* | ATCC 27957 |
|  | *Streptococcus uberis* | ATCC 27958 |
|  | *Pseudomonas aeruginosa* | ATCC 15442 |

| Test Temperature: | Ambient temperature |
|---|---|
| Exposure Time: | 15 seconds |
| Neutralizer: | Chambers |
| Subculture Media: | Tryptone Glucose Extract Agar |
|  | Brain Heart Infusion Agar (for *Streptococci*) |
| Incubation: | 37° C. for 48 hours |

Results:

Inoculum Numbers (CFU/mL)

| Organism | Date | A | B | C | Average |
|---|---|---|---|---|---|
| *S. aureus* ATCC 6538 | 7/18/00 | $94 \times 10^6$ | $91 \times 10^6$ | $90 \times 10^6$ | $9.2 \times 10^7$ |
| *E. coli* ATCC 11229 | 6/29/00 | $115 \times 10^6$ | $105 \times 10^6$ | $102 \times 10^6$ | $1.1 \times 10^8$ |
| *E. aerogenes* ATCC 13048 | 6/29/00 | $70 \times 10^6$ | $66 \times 10^6$ | $64 \times 10^6$ | $6.7 \times 10^7$ |
| *Klebsiella pneumoniae* ATCC 4352 | 7/18/00 | $168 \times 10^6$ | $176 \times 10^6$ | $126 \times 10^6$ | $1.6 \times 10^8$ |
| *Streptococcus agalactiae* ATCC 27956 | 6/29/00 | $36 \times 10^6$ | $58 \times 10^6$ | $28 \times 10^6$ | $4.1 \times 10^7$ |
| *Streptococcus dysgalactiae* ATCC 27957 | 7/18/00 | $74 \times 10^6$ | $59 \times 10^6$ | $44 \times 10^6$ | $5.9 \times 10^7$ |

-continued

| Organism | Date | A | B | C | Average |
|---|---|---|---|---|---|
| *Streptococcus uberis* ATCC 27958 | 7/18/00 | $67 \times 10^6$ | $76 \times 10^6$ | $38 \times 10^6$ | $6.0 \times 10^7$ |
| *Pseudomonas aeruginosa* ATCC 15442 | 7/18/00 | $84 \times 10^6$ | $163 \times 10^6$ | $134 \times 10^6$ | $1.3 \times 10^8$ |

Test Results

| Test Substance | Test Organism | Survivors (CFU/mL) | Average Survivors (CFU/mL) | Log Reduction | Percent Reduction |
|---|---|---|---|---|---|
| KX-6128 | *S. aureus* | <10, <10 | <10 | >6.96 | >99.999 |
| KX-6128 | *E. coli* | <10, <10 | <10 | >7.04 | >99.999 |
| KX-6128 | *E. aerogenes* | <10, <10 | <10 | >6.83 | >99.999 |
| KX-6128 | *K. pneumoniae* | <10, <10 | <10 | >7.20 | >99.999 |
| KX-6128 | *S. agalactiae* | <10, $2.0 \times 10^1$ | $1.5 \times 10^1$ | >6.61 | >99.999 |
| KX-6128 | *S. dysgalactiae* | <10, <10 | <10 | >6.77 | >99.999 |
| KX-6128 | *S. uberis* | <10, <10 | <10 | >6.78 | >99.999 |
| KX-6128 | *P. aeruginosa* | <10, <10 | <10 | >7.11 | >99.999 |

Conclusions:

Teat Dip Formulation 1 (from table 1) achieved a >99.999 percent reduction with a 15 second exposure time at ambient temperature against *Staphylococcus aureus* ATCC 6538, *Escherichia coli* ATCC 11229, *Enterobacter aerogenes* ATCC 13048, *Klebsiella pneumoniae* ATCC 4352, *Streptococcus agalactiae* ATCC 27956, *Streptococcus dysgalactiae* ATCC 27958, *Streptococcus uberis* ATCC 27958, and *Pseudomonas aeruginosa* ATCC 15442. This percent reduction was unexpectedly high.

From the foregoing detailed description and examples, it will be evident that modifications and variations can be made to the compositions and methods of the invention without departing from the spirit and scope of the invention. Therefore, it is intended that all modifications made to the invention without departing from the spirit and scope of the invention come within the scope of the appended claims.

What is claimed is:

1. A heptanoic acid antimicrobial composition comprising:
   0.01 to 5 wt. % heptanoic acid;
   greater than 60 wt. % of a freezing point depressant component comprising propylene glycol and glycerin and a carrier medium.

2. The antimicrobial composition of claim 1, wherein the freezing point depressant component consists of a mixture of propylene glycol and glycerin.

3. The antimicrobial composition of claim 1, wherein the composition has a freezing point of below 32° F.

4. The antimicrobial composition of claim 1, wherein the composition has a freezing point of below 20° F.

5. The antimicrobial composition of claim 1, wherein the composition has a freezing point of below 10° F.

6. The antimicrobial composition of claim 1, wherein the composition has a freezing point of below 0° F.

7. The antimicrobial composition of claim 1, wherein the composition has a freezing point of below −10° F.

8. The antimicrobial composition of claim 1, wherein the composition has a freezing point of below −20° F.

9. The antimicrobial composition of claim 1, wherein the freezing point depressant component makes up greater than 65 wt. % of the composition.

10. The antimicrobial composition of claim 1, wherein the freezing point depressant component makes up greater than 70 wt. % of the composition.

11. The antimicrobial composition of claim 1, wherein the freezing point depressant component makes up greater than 75 wt. % of the composition.

12. A method for controlling mastitis in milk producing animals, the method comprising:
   applying a heptanoic acid antimicrobial composition to a teat of a milk producing animal, wherein the heptanoic acid antimicrobial composition comprises:
   0.01 to 5 wt. % heptanoic acid;
   greater than 60 wt. % of a freezing point depressant component comprising propylene glycol and glycerin and a carrier medium.

13. The method of claim 12, wherein the antimicrobial composition is applied in environmental temperatures of below 40° F. or is applied to the teat of the milk producing animal that will be exposed to environmental temperatures of below 40° F. within 12 hours of the application.

14. The method of claim 13, wherein the environmental temperatures are below 30° F.

15. The method of claim 13, wherein the environmental temperatures are below 20° F.

16. The method of claim 13, wherein the environmental temperatures are below 10° F.

17. The method of claim 12, wherein the freezing point depressant component consists of a mixture of propylene glycol and glycerin.

18. The method of claim 12, wherein the composition has a freezing point of below 32° F.

19. The method of claim 12, wherein the composition has a freezing point of below 20° F.

20. The method of claim 12, wherein the composition has a freezing point of below 10° F.

21. The method of claim 12, wherein the composition has a freezing point of below 0° F.

22. The method of claim 12, wherein the composition has a freezing point of below −10° F.

23. The method of claim 12, wherein the composition has a freezing point of below −20° F.

24. The method of claim 12, wherein the freezing point depressant component makes up greater than 65 wt. % of the composition.

25. The method of claim 12, wherein the freezing point depressant component makes up greater than 70 wt. % of the composition.

26. The method of claim 12, wherein the freezing point depressant component makes up greater than 75 wt. % of the composition.

27. The antimicrobial composition of claim 1, wherein the freezing point depressant component consists essentially of a mixture of propylene glycol and glycerin.

28. The method of claim 12, wherein the freezing point depressant component consists essentially of a mixture of propylene glycol and glycerin.

29. The antimicrobial composition of claim 1, further comprising rheology modifier, lanolin, surfactant, sequestrant, or mixture thereof.

30. The method of claim 12, wherein the composition further comprises rheology modifier, lanolin, surfactant, sequestrant, or mixture thereof.

* * * * *